US007587384B2

(12) United States Patent
Vadrot et al.

(10) Patent No.: US 7,587,384 B2
(45) Date of Patent: Sep. 8, 2009

(54) SYSTEM OF MANAGEMENT OF INFORMATION FOR EMERGENCY SITUATIONS

(75) Inventors: Dominique Vadrot, Fontenay Sous Bois (FR); Martine Verdoux, Paris (FR)

(73) Assignee: Patient On Line, Paris (FR)

( * ) Notice: Subject to any disclaimer, the term of this patent is extended or adjusted under 35 U.S.C. 154(b) by 559 days.

(21) Appl. No.: 10/456,561

(22) Filed: Jun. 9, 2003

(65) Prior Publication Data

US 2003/0233342 A1    Dec. 18, 2003

(30) Foreign Application Priority Data

Jun. 18, 2002    (FR)    .................................... 02 07499

(51) Int. Cl.
*G06F 7/00* (2006.01)
(52) U.S. Cl. ................. 707/2; 707/1; 707/10; 707/100; 707/200; 707/104.1; 705/2; 705/3
(58) Field of Classification Search ..................... 707/2, 707/10, 200; 705/2, 3
See application file for complete search history.

(56) References Cited

U.S. PATENT DOCUMENTS 6,073,106 A * 6/2000 Rozen et al. ................... 705/3

| 6,463,417 | B1 * | 10/2002 | Schoenberg | 705/2 |
| 6,775,670 | B2 * | 8/2004 | Bessette | 707/10 |
| 2002/0029157 | A1 * | 3/2002 | Marchosky | 705/3 |
| 2002/0046346 | A1 * | 4/2002 | Evans | 713/200 |
| 2003/0074564 | A1 * | 4/2003 | Peterson | 713/182 |

FOREIGN PATENT DOCUMENTS

| FR | 2 704 336 | 10/1994 |
| WO | WO 01/55949 | 8/2001 |
| WO | WO 01/63538 | 8/2001 |
| WO | WO 01/69514 | 9/2001 |

\* cited by examiner

*Primary Examiner*—Hung Q Pham
(74) *Attorney, Agent, or Firm*—Young & Thompson

(57) ABSTRACT

A system including at least one database for the storage of items of information, and an identifier of a first entity concerned by each item of information; and at least one interrogation station comprising elements for access to the database, there being elements for defining items of warning information amongst the items of information and elements for associating an emergency access code with the items of warning information. The access elements include elements for input of the emergency access code and elements for making available the warning information concerning a first entity without the identifier of the first entity being made available.

6 Claims, 4 Drawing Sheets

SYSTEM OF MANAGEMENT OF INFORMATION FOR EMERGENCY SITUATIONS

TECHNICAL FIELD

The present invention relates to a system for the management of information, and in particular medical information, each item of information concerning a first entity, the system comprising:
- at least one database for the storage of:
  - the said items of information;
  - an identifier of the first entity concerned by each item of information, each item of information being associated with the identifier of the first entity concerned; and
- at least one interrogation station comprising means for access to the or each database for the consultation of the said items of information.

BACKGROUND TO THE INVENTION

In numerous fields it is necessary to be able to ensure confidential storage and authorised and controlled consultation of validated items of information concerning a person.

These items of information may be for example medical information concerning a patient. These items of medical information are generated by one or several medical practitioners subject to the obligations of a professional code of ethics. In particular, these obligations impose upon the practitioners the respect for professional confidentiality, such that practitioners are forbidden to make this information accessible without the authorisation of the patient concerned and the patient must be able to access the information concerning him.

The obligations of the professional codes of ethics of the practitioners make it difficult to exploit the data concerning the patient in an emergency. In particular, if the patient becomes ill on the public highway the emergency services taking charge of the patient cannot directly access the medical information concerning the patient if this emergency service has not previously been authorised to access these items of information and if the patient is not necessarily easily identifiable, particularly if he is unconscious.

The object of the invention is to propose a system of management of information which permits useful items of information to be made accessible, even when the person concerned by the items of information is not conscious, whilst guaranteeing that the obligations of the professional code of ethics are respected.

SUMMARY OF THE INVENTION

To this end, the invention relates to a system of management of information of the aforementioned type, characterised in that it comprises:
- means for defining items of warning information amongst the said items of information;
- means for associating an emergency access code with the items of warning information concerning one and the same first entity, the emergency access code being different from the identifier of the first entity;

and in that the said access means comprise means for input of the emergency access code and means for, at the time of input of the emergency access code associated with the identifier of a first entity, making available the items of warning information concerning the first entity associated with the emergency access code, without the identifier of the first entity being made available.

According to particular embodiments, the system for management of information comprises one or several of the following characteristics:
- it comprises:
  - means for creating at least one event bringing together in an indissociable manner in one and the same data item:
    - the or each item of information concerning the first entity; and
    - the identifier of the first entity; and
  - means for definitive storage of the content of the or each event, each by way of a data item in the or each database;
- the means for defining items of warning information amongst the items of information include:
  - means for fixing, for each item of information, a warning indicator representing the definition of the items of information;
  - means for integrating the warning indicator representing the definition of the items of information into the data item corresponding to the event containing the said item of information; and
  - means for integrating the warning indicator into the data item corresponding to the event containing the said item of information, and the said means for making the items of warning information available comprise means for analysis of the warning indicator contained in each event containing the identifier of the first entity associated with the emergency access code, and the means for making the items of warning information available are adapted to make available the or each item of information contained in the event, if the analysis of the warning indicator shows that the or each item of information is an item of warning information;
- the system comprises means for integrating into each data item corresponding to an event an identifier of a second entity who has generated the said item of information;
- the said means for associating an emergency access code with the items of warning information concerning one and the same entity comprising a data base which establishes a correspondence between each emergency access code and an identifier of a first entity; and
- the system comprises means for random generation of an emergency access code for each new identifier of a first entity.

The invention also relates to a method of management of information, each item of information concerning a first entity in a system comprising:
- at least one database for the storage of:
  - the said items of information;
  - an identifier of the first entity concerned by each item of information, each item of information being associated with the identifier of the first entity concerned; and
- at least one interrogation station comprising means for access to the or each database for the consultation of the said items of information, and
- means for defining items of warning information amongst the said items of information, and in which an emergency access code is associated with the items of warning information concerning one and the same first entity, the emergency access code being different from the identifier of the first entity, characterised in that it comprises the input from the said access means of an emergency access code and, at the time of input of the emergency access code associated with the identifier of a first entity, making available the items of warning information concerning the first entity associated with the emergency access code, without the identifier of the first entity being made available.

BRIEF DESCRIPTION OF DRAWINGS

The invention will be better understood by reading the description which follows, given solely by way of example and with reference to the drawings, in which.

DESCRIPTION OF PREFERRED EMBODIMENT

Figure 1:
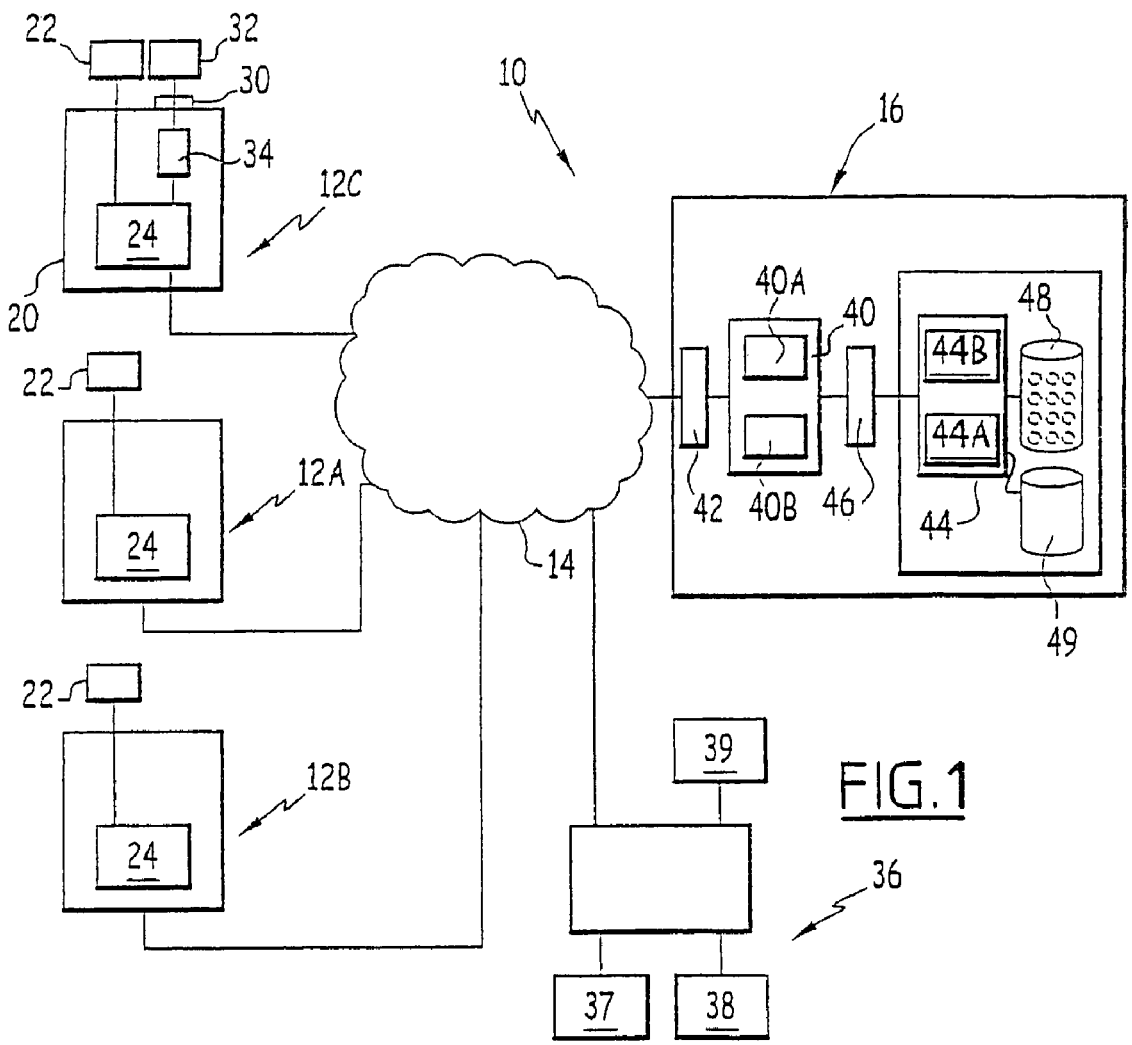
FIG. 1 is a schematic view of a system for the management of information according to the invention.

The system for the management of information 10 according to the invention is illustrated schematically in FIG. 1. This comprises, on the one hand, a set of user stations designated by the general reference 12, each connected to a collective information transmission network 14 such as the Internet and, on the other hand, a centre 16 for storage and management of information.

The system for the management of information 10 is intended, in the example under consideration, for the management of medical information concerning identified patients. These items of information are generated by medical practitioners such as doctors, radiologists or biologists in charge of an analysis laboratory.

In particular the management system is adapted to permit the definitive storage of an item of information in the storage centre 16 without it being possible for this item of information to be modified subsequently. Furthermore, at least one identifier of the patient concerned, as well as an identifier of the practitioner who generated the item of information, is preserved, associated with this item of information.

The system permits access to a stored item of information from the identifier of the patient to be given solely to the patient concerned and to the practitioner who generated the item of information, as well as, possibly, after the patient's agreement, to other practitioners.

Furthermore, the system permits access to certain stored items of information concerning a patient by persons having an emergency access code. The items of information are then made available in a reduced number and without the identifier of the patient concerned by these items of information being made available.

Each entity entering into the system, whether they be a patient or a practitioner, is equipped with or has access to a user station 12. Thus, for example, a first user station 12A serves the consulting-room of a general medical practitioner and a user station 12B serves the home of a patient. Likewise, for example, a medical imaging laboratory is equipped with a user station 12C.

Each user station 12A, 12B, 12C has a microcomputer 20 equipped with an adapted Internet navigator. It is connected by an adapted interface to the network 14. Each user station includes means 22 for collection of input data such as a keyboard or a data conversion module. From the keyboard it is possible to input in particular an item of medical information, an identifier of a patient such as his name, as well as an identifier of the practitioner who produced the item of information.

Each user station 12 is adapted to implement, from information processing means 24, software means for access to the centre 16 for storage and management of information.

According to the invention, each user station 12A, 12B, 12C has software means in order to create an event bringing together, in an indissociable manner in one and the same data item, items of information collected concerning a patient, an identifier of the patient and an identifier of the practitioner. These means for creation of an event are advantageously downloaded from the centre 16 and consist for example of a page in HTML (Hyper Text Markup Language) format forming a dialogue interface.

Certain of these user stations, such as the station 12C, have in addition to the microcomputer 20 an interface 30 for connection of the microcomputer to an installation 32 for medical imaging or for collecting medical information capable of producing images or digital items of information in a predefined format such as the format DICOM Hprim HL7. By its nature, this image or digital item of information includes an identifier of the patient concerned. The user station also implements a software module 34 adapted to analyse the digital image produced by the installation 32 and to extract from the latter an identifier of the patient concerned.

Furthermore, the system comprises interrogation stations 36 connected to the centre 16 for storage and management of information via the network 14. Each interrogation station 36 is formed by any microcomputer 20 equipped with an adapted internet navigator. These interrogation stations have not been identified initially by the centre for storage and management of information 16.

Each interrogation station 36 comprises means for input of an emergency access code, such a s keyboard 37, or a chip card reader 38 as well as a peripheral for making information available such as a screen or a printer 39.

The centre for storage and management of information 16 includes a set of servers 40 for the management of access to the centre 16. This set of servers 40 includes in particular an authentication server 40A adapted, as is known per se, to identify the origin of a request addressed to the server centre. It also includes one or several servers 40B adapted to the management of the exchange of executable files and of HTML pages according to the HTTP protocol between the centre for storage and management 16 and the user stations. In particular, the or each server 40B includes a software module adapted to ensure the downloading in each requesting user station of HTML pages constituting user interfaces permitting access to the stored information, as well as the saving of new items of information. This set of servers 40 is connected directly to the network 14 via a first security barrier 42 (firewall).

The set of servers for management of access 40 is also connected to a set of servers 44 for management of events via a second security barrier 46 (firewall). In particular, the set of servers 44 is adapted to implement a software module 44A for transcription of the digital images received in formats different in particular from the DICOM format into one and the same format, for example the XML format.

The set of servers 44 is also adapted to implement a software module 44B for management of the storage of events in a unit 48 for storage and management of access to these events.

This storage unit 48 is intended for the permanent memorisation of one or several databases, the data items of which are constituted by events defined by the user stations and include in particular the items of information to be saved.

Furthermore, a supplementary storage unit 49 is connected to the set of servers 44. This storage unit is intended for the permanent memorisation of a database in which an associated emergency access code is stored for each identifier of a patient concerned by items of information.

The emergency access code is defined randomly by the module for management 44B for each new patient managed by the system. The code is different from the identifier of the patient such as his surname.

The access code is written on a card which is given to the patient. The IP address of the centre 16 for storage and management of information is also given on this card.

As a variant, the emergency access code is memorised in a memory card which can be read in a card reader of a computer. This card also bears the IP address of the centre 16.

Figure 2:
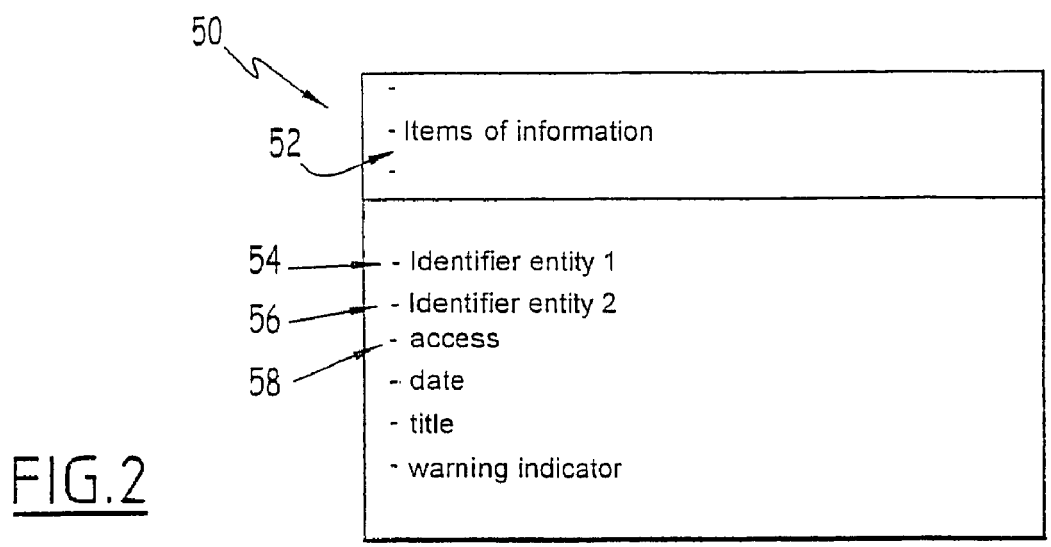
FIG. 2 is a schematic view illustrating the format of a data item used by the system for the management of information shown in FIG. 1.

The structure of a data item stored in the database 48 is represented schematically in FIG. 2. This data item corresponds to an event.

Each event comprises at least one actual item of information 52. This item of information is constituted for example by digital data corresponding to the result of an analysis or by a text corresponding to the opinion of a practitioner on the clinical condition of a patient. An item of information may equally be constituted by a file attached to the event such as a document in HTML format or an image file in DIBCOM format or an attachment in an office administration format.

Furthermore, each event includes an identifier 54 of a first entity. This identifier designates the patient concerned by the items of information 52. Likewise, the event includes an identifier 56 of a second entity. This identifier designates the practitioner who produced the item of information.

Each event advantageously includes a list 58 of identifiers of additional entities which can have access to the information.

The event also includes, advantageously but not obligatorily, other items of information to be filled in by the user such as:
  a title;
  a date of creation and/or of supplements to the event; and
  a list of keywords.

Furthermore, each event comprises a warning indicator consisting of a boolean indicator indicating in its first state (valid) that the items of information contained in the event constitute items of warning information which can be communicated in an emergency, and in its second state (invalid) that the items of information contained in the event must not be communicated in an emergency.

For adding an item of information in the storage centre, complementing a pre-existing item of information with a supplementary item of information, modification of the rights of access to an item of information or consulting an item of information, the user connects from a user station 12 to the storage centre 16.

Figure 3:
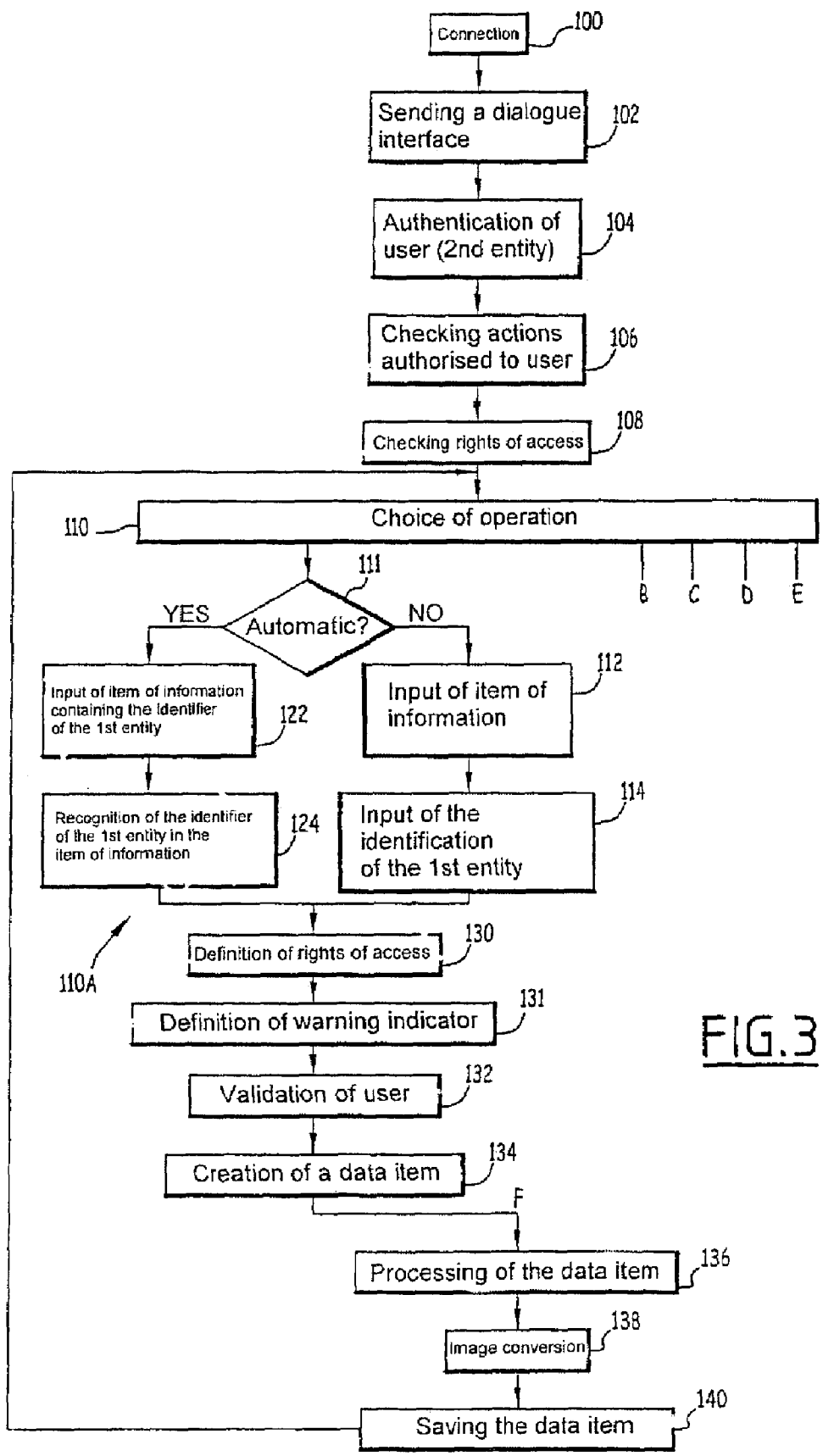
FIG. 3 is a flow chart of the principal algorithm implemented in the system.
Figure 3:
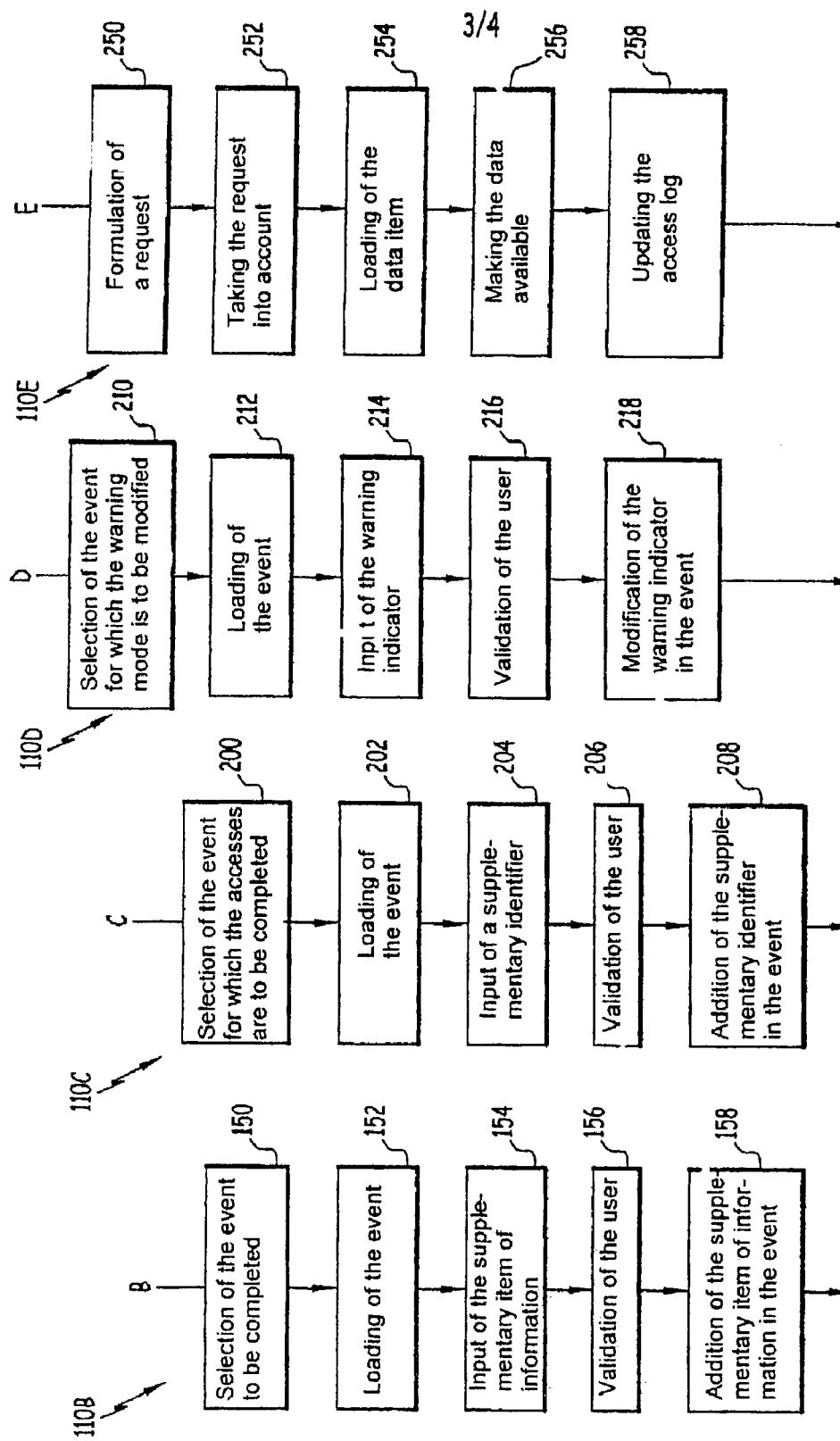

The algorithm of FIG. 3 is then implemented.

The user station can be constituted, for the simplest operations, solely by a microcomputer connected to the Internet with the aid of a navigator of any adapted type. After connection of the user station, at step 100, the set of servers 40 of the storage centre 16 returns a dialogue interface in HTML format to the user station 12, at step 102. At step 104, the centre 16 proceeds via the dialogue interface implemented by the user station with an authentication of the user. As a function of the identifier input by the user, checks of the actions authorised for this user are carried out, at step 106, and a check of the access rights of the user is carried out, at step 108.

The user is then free to proceed with several operations as a function of the actions which are authorised for him. From the interface made available to him he proceeds, at step 110, with the choice of an operation to carry out.

This may be the input of a new item of information into the storage centre 16. The branch 110A of the flow chart is then implemented.

It may equally be the addition of a supplementary item of information in order to complete an item of information already present in the storage centre 16. The branch 110B of the flow chart is then implemented.

The practitioner user can equally modify the rights of access to the items of information stored by authorising a new practitioner to access the information concerning a patient. The branch 110C of the flow chart is then implemented.

When the practitioner wishes to modify the warning indicator of an event, the branch 110D of the algorithm is implemented.

Equally, the user can simply gain knowledge of items of information stored in the storage centre by implementation of the branch 110E of the flow chart.

When a practitioner wishes to input a new item of information into the centre 16, the algorithm differs according to whether the item of medical information which the practitioner wishes to input can be associated automatically with a patient constituting the first entity or whether the connection with the patient must be effected manually. This choice is effected at step 111.

If the item of information does not initially contain the identifier of the patient concerned, the item of information is input by the practitioner, for example at the keyboard, at step 112. An identification of the patient concerned is entered, at step 114, particularly by selection of an identifier of the patient from among a list of identifiers of patients or by keystrokes.

By contrast, and in the case of a user station such as the station 12C, the recognition of the identifier of the patient concerned can be achieved automatically at the time of input of the item of information. Thus, the item of information containing the identifier of the patient concerned is input, at step 122, for example via the interface 30. This information is constituted for example by a medical image in DICOM format. At step 124, the software module 36 proceeds to an analysis of the image and a recognition of the identifier of the patient in the image transmitted.

At step 130, the practitioner defines the list of identifiers of the supplementary entities authorised to access the items of information contained in the event. This step consists of defining the list 58 of identifiers of the practitioners authorised to have access.

At step 131, the practitioner defines the warning indicator by specifying whether the item of information contained in the event may or may not be made accessible in an emergency according to a procedure described later in the description.

If the practitioner wishes to make this item of information accessible in an emergency, he ensures that the item of information in itself does not contain data which make it possible to identify the patient, such as his surname.

At step 132, the practitioner validates by entry of a signature code all of the elements constituting the event, namely the actual item of medical information, the identifier of the patient concerned, his own identifier, the list of identifiers of the supplementary entities authorised to have access, and the warning indicator. At the end of this step, the elements constituting the event can no longer be modified and the event can only be completed.

At step 134, the user station 12 ensures the creation of a data item including the different elements of the event. This data item is encrypted by any suitable process and is addressed by the dialogue interface to the centre 16 for storage and management of information.

Upon its reception, the data item is processed by the servers for management of events 44, at step 136. If the data item contains digital images in formats different from XML format, these images are automatically converted to XML format, at step 138, and the data item is completed by image data in XML format in addition to the image data in another format.

The data item thus reprocessed is saved definitively in the storage unit 48, at step 140.

When the user wishes to complete an event by adding a supplementary item of information, the steps of the branch 110B are implemented after step 110.

At step 150, the event to be completed is selected.

The data item corresponding to the event selected is transmitted by the centre 16 to the user station, at step 152. The data item is only transmitted if the identifier of the user is included in the event in question, whether it be the patient concerned, the practitioner who originated the item of information or a supplementary practitioner whose identifier appears in the list 58.

The supplementary item of information is input at step 154, either manually from the keyboard or by resumption of an already existing file. In this latter case the supplementary item of information constitutes a new attached file.

At step 156, the user validates the addition of information by input of a signature code.

The supplementary item of information is added at step 158 to form a new data element constituting the modified event. Furthermore, the date and the identifier of the user who added the item of information, as well as a link to the item of information are added in the data item in order to follow through the modifications. The new data item thus constituted is then processed in accordance with steps 136 and following.

When the user wishes to modify a right of access, he can solely add new user identifiers authorised to access a given item of information. To this end, the event for which the accesses are to be completed is selected at step 200. The data item corresponding to the selected event is then transmitted to the user station at step 202. The data item is only transmitted if the identifier of the user is included in the event in question, whether it be the patient concerned, the practitioner who originated the item of information or an additional practitioner whose identifier appears in the list 58.

At step 204, the user selects or enters at the keyboard one or several additional identifiers of users authorised to access the item of information then, at step 206, he validates the new identifiers. The supplementary identifiers are added in the data item constituting the event at step 208. Furthermore, the date and the identifier of the user who added the item of information, as well as a link to the new identifiers are added in the data item in order to follow through the modifications. The steps 136 and following are then implemented again.

When the user, and particularly the practitioner wishes to modify the warning indicator associated with an item of information in order to make this item of information accessible in an emergency, or on the contrary not to make this item of information accessible, the branch 110D of the algorithm is implemented.

At step 210, the event of which the warning indicator is to be modified is selected. The data item corresponding to the selected event is transmitted to the user station 12 at stem 212, provided that the identifier of the user is included in the event in question because it relates to the patient concerned, the practitioner who originated the item of information or a supplementary practitioner whose identifier appears in the list 58.

At step 214, the user changes the state of the warning indicator, for example by validation on the screen of a predefined zone. If the practitioner wishes to make this item of information accessible in an emergency, he ensures that the item of information in itself does not contain data which would make it possible to identify the patient, such as his surname. The modified event is then validated at step 216.

The new value of the warning indicator is added into the data item which constitutes the event at step 218.

Furthermore, the date and the identifier of the user who modified the warning indicator are added into the data item in order to follow through the modifications.

The steps 136 and following are then implemented again.

For consultation of the items of information stored in the centre 16, and from any user station whatsoever, the steps of the branch 110E are implemented.

At step 250, a request is formulated by the user from the user station. This is taken into account by the servers for management of the events 44, at step 252. As a function of the rights of access contained in the event in question in the request, and as a function of the rights of the user, the content of the data item is transmitted from the storage centre 16 to the user station 12, at step 254.

In particular, the data item is only transmitted if the identifier of the user is included in the event in question in the request, whether it be the patient concerned, the practitioner who originated the item of information or an additional practitioner whose identifier appears in the list 58.

The item of information is then made available to the user at step 256, for example by display, or by saving the content of the data item on the hard disk of the user station.

At step 258 a log of the accesses is updated in the centre 16 in order to record the identifier of the user, the nature of the information made available, the date of access provided by the system and any other useful information.

In order to make it possible in an emergency for the necessary items of information to made accessible to the emergency services, whether or not these are health practitioners, the patient whose information is stored in the system carries with him the card bearing the IP address of the centre 16 for management and storage of information on the network 14, as well as the emergency access code associated with the patient.

Figure 4:
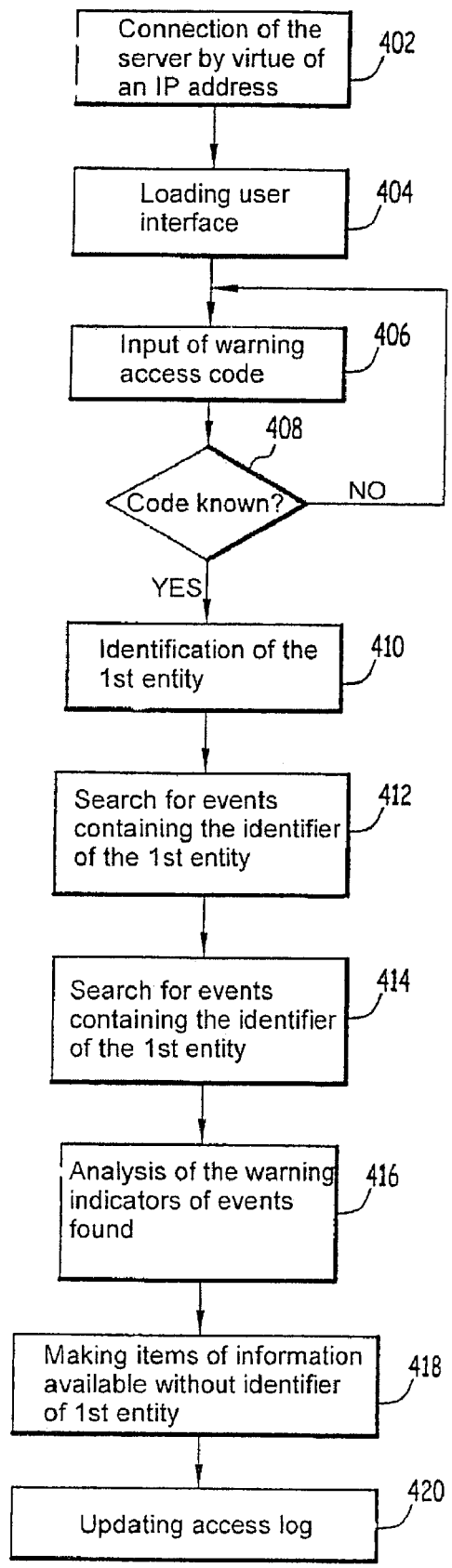
FIG. 4 is a flow chart of the algorithm for emergency consultation of the system according to the invention.

In order to permit access to the items of warning information, the algorithm of FIG. 4 is implemented.

When the patient requires medical care, even though he is not with a practitioner authorised to access the items of information, the patient can give to any questioner the card which he carries with him in order to permit his questioner to access certain items of warning information which the patient has previously selected by putting the warning indicators associated with these items of information into a predetermined valid state or having them put into a valid state.

In the event that the patient is unconscious, the emergency services can take the card carried by the patient and can collect the items of emergency information themselves.

To this end, at step 402, the emergency service connects to the centre 16 for storage and management of information by virtue of the IP address mentioned on the card carried by the patient. This connection may be effected from any computer connected to the network 14 and having an adapted internet navigator. This computer then forms an interrogation station 36.

After connection, at step 404 the centre 16 ensures the loading of a user interface in the interrogation station 36. At step 406, the emergency service is invited to enter the emergency access code specific to the patient. As this emergency access code being totally independent of the identifier of the patient, the identifier of the patient is not necessary for the input of the warning code.

The software module 44B for management of the access to the stored events determines at step 408 whether or not the emergency access code is associated with a known identifier, by interrogation of the database accommodated in the storage unit 49.

If the warning access code is unknown, step 406 is implemented again.

On the other hand, if the warning access code is known, at step 410 the centre 16 for storage and management of information determines the identifier of the patient concerned.

At step 412, the software module 44B for management of the events searches among the stored events for the events containing the identifier of the first entity. Amongst these events found, at step 414 it analyses the warning indicator associated with each event. It selects from amongst the events those of which the warning indicators are in a valid state indicating that the items of information contained in the event can be communicated in an emergency.

At step 416, the centre 16 ensures the transmission without encryption of the items of information contained in each of the sole events of the base 48 in respect of which the warning indicator is valid and in respect of which the identifier of the first entity is the identifier associated with the warning access code in the base 49.

The items of information transmitted are communicated without the identifier of the first entity being transmitted.

At step 418, the items of information transmitted are made available to the emergency service, for example by display of these items of information on the screen of the interrogation station 36.

At step 420, a log of the accesses is updated in the centre 16 by recording the nature of the information made available, the date of access provided by the system and any other useful information.

It will be understood that with such a system for the management of information, items of information useful for the treatment of the patient in an emergency can be made available to any emergency service without the identity of the patient being revealed, and by permitting only the necessary items of information previously selected with the agreement of the patient to be transmitted to the emergency service at the time of their intervention.

Furthermore, the access to these items of information is very simple and is made possible even if the emergency service is not normally authorised to enter the system and even if the patient is unconscious.

The invention claimed is:

1. System for the management of patient medical information, the system comprising:
   means for creating data items, each created data item comprising elements brought together in an indissociable manner, the elements comprising i) an information item concerning a patient, ii) an identifier of the patient, the information item being indissociable from the identifier of the patient, and iii) an identifier of a practitioner who generated the data item, the information item being indissociable from the identifier of the practitioner;
   means for defining items of warning information amongst said created data items;
   means for associating an emergency access code of a first patient with the defined items of warning information corresponding to the first patient, wherein the emergency access code is associated with the identifier of the first patient but is different from the identifier of the first patient, and is totally independent of the identifier of the first patient;
   means for validating of said created data items by the practitioner, wherein said elements of the created data item after validation can no longer be modified and the validated data item can only be supplemented by the addition of supplemented items of information constituting new elements of the validated data item; and
   means for definitively storing said validated data items in a database;
   means for accessing to the database for stored data item of the first patient, wherein the stored data item of the first patient is accessed solely by an entity among the first patient and the practitioner, and one who is authorized by the first patient and the practitioner, wherein authorization information of the authorized one is included in the stored data item containing information item of the first patient;
   an interrogation station comprising an access means to access the database for said defined items of warning information;
   said access means comprising i) input means to input the emergency access code associated with the identifier of the first patient and ii) means for, at the time of input of the emergency access code associated with the identifier of first patient, making available the items of warning information corresponding to the first patient associated with the input emergency access code, without the identifier of the first patient being made available.

2. System for the management of patient medical information, as claimed in claim 1, wherein, the means for defining items of warning information include:
   means for fixing, for each information item, a warning indicator representing the definition of the information item;
   means for integrating the warning indicator into the corresponding stored data item; and
   said means for making the items of warning information available comprise means for analyzing of the warning indicator contained in each data item containing the identifier of the patient associated with the emergency access code, and
   said means for making the items of warning information available are adapted to make available each information item concerning the patient contained in the data item, if the analysis of the warning indicator shows that the information item is an item of warning information.

3. System for the management of patient medical information as claimed in claim 1, wherein, said created data item further comprises an identifier of an second entity who has generated said information item.

4. System for the management of patient medical information as claimed in claim 1, wherein said means for associating an emergency access code with the defined items of warning information comprise a database which establishes a correspondence between each emergency access code and an identifier of patient.

5. System for the management of patient medical information as claimed in claim 1, further comprising a random generator of the emergency access code.

6. Method for the management of patient medical information, comprising the steps consisting of:
creating data items, each created data item comprising elements brought together in an indissociable manner, the elements comprising i) an information item concerning a patient, ii) an identifier of the patient, the information item being indissociable from the identifier of the patient, and iii) an identifier of a practitioner who generated the data item, the information item being indissociable from the identifier of the practitioner;
defining items of warning information amongst said created data items;
associating an emergency access code of a first patient with the defined items of warning information corresponding to the first patient, wherein the emergency access code being associated with the identifier of the first patient but being different from the first identifier of the first patient, and being totally independent of the identifier of the first patient;
validating said created data items by the practitioner, wherein said elements of the created data item after validation can no longer be modified and the validated data item can only be supplemented by the addition of supplemented item of information constituting new elements of the validated data item; and
definitively storing said validated data items in a database;
accessing said defined items of warning information by:
inputting the emergency access code associated with the identifier of the first patient;
making available the items of warning information corresponding to the first patient associated with the input emergency access code, at the time of input of the emergency access code associated with the identifier of first patient, without the identifier of the first patient being made available;
accessing to the database for stored data item of the first patient, wherein the data item of the first patient is accessed solely by an entity among the first patient and the practitioner, and one who is authorized by the first patient and the practitioner, wherein authorization information of the authorized one is included in the stored data item containing information item of the first patient.

* * * * *

UNITED STATES PATENT AND TRADEMARK OFFICE
CERTIFICATE OF CORRECTION

PATENT NO. : 7,587,384 B2  Page 1 of 1
APPLICATION NO. : 10/456561
DATED : September 8, 2009
INVENTOR(S) : Vadrot et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 751 days.

Signed and Sealed this

Twenty-first Day of September, 2010

David J. Kappos
*Director of the United States Patent and Trademark Office*